United States Patent [19]

Kole et al.

[11] Patent Number: 5,627,274

[45] Date of Patent: May 6, 1997

[54] ANTISENSE OLIGONUCLEOTIDES WHICH COMBAT ABERRANT SPLICING AND METHODS OF USING THE SAME

[75] Inventors: Ryszard Kole; Zbigniew Dominski, both of Chapel Hill, N.C.

[73] Assignee: The University of North Carolina at Chapel Hill, Chapel Hill, N.C.

[21] Appl. No.: 453,224

[22] Filed: May 30, 1995

Related U.S. Application Data

[62] Division of Ser. No. 379,079, Jan. 26, 1995, which is a continuation of Ser. No. 62,471, May 11, 1993, abandoned.

[51] Int. Cl.$^6$ .......................... C07H 21/00; A61K 48/00; C12Q 1/68

[52] U.S. Cl. .................. 536/23.1; 536/24.3; 536/24.31; 536/24.33; 536/24.5; 435/6; 424/450

[58] Field of Search .......................... 514/44; 536/24.5, 536/23.1, 24.1, 24.3, 24.31, 24.33; 935/34, 44, 62, 78, 33, 3, 6, 8, 9; 435/6, 240.2; 424/450

[56] References Cited

U.S. PATENT DOCUMENTS

| | | | |
|---|---|---|---|
| 5,023,243 | 6/1991 | Tullis | 514/44 |
| 5,149,797 | 9/1992 | Pederson et al. | 536/27 |
| 5,220,007 | 6/1993 | Pederson et al. | 536/23.1 |

OTHER PUBLICATIONS

S.H. Munroe; Antisense RNA inhibits splicing of pre-mRNA in vitro; *The EMBO Journal 7*, pp. 2523–2532 (1988).

P.J. Furdon and R. Kole; Inhibition of In Vitro Pre–mRNA Splicing by Antisense Deoxyoligonucleotide Analogues, *Journal of Cellular Biochemistry* Abstracts 18th Annual Meetings, (Mar. 27–Apr. 7, 1989).

Y. Zhuang and A.M. Weiner; A compensatory base change in human U2 snRNA can suppress a branch site mutation, *Genes & Development 3*, pp. 1545–1552 (1989).

V. Volloch et al; Inhibition of Pre–mRNA Splicing by Antisense RNA In Vitro: Effect Of RNA Containing Sequences Complementary to Exons, *Biochemical and Biophysical Research Communications 179*, pp. 1593–1599 (1991).

C.F. Bennett et al; Cationic Lipids Enhance Cellular Uptake and Activity of Phosphorothioate Antisense Oligonucleotides *Molecular Pharmacology 41*, pp. 1023–1033 (1992).

Z. Dominski and R. Kole; Restoration of correct splicing in thalassemic pre–mRNA by antisense oligonucleotides *Proc. Natl. Acad. Sci. 90* pp. 8673–8677 (1993).

R. Kole et al.; Pre–mRNA splicing as a target for antisense oligonucleotides. *Advance Drug Delivery Reviews 6*, 271–286 (1991).

Ryder et al.; Sequence–specific affinity selection of mammalian splicing complexes. *Nucleic Acids Research 18*(24), 7373–7374 (1990).

Furdon et al.; RNase H cleavage of RNA hybridized to oligonucleotides containing methylphosphonate, phosphorothioate and phosphodiester bonds. *Nucleic Acids Research 17*(22), 9192–9204 (1989).

Ruskin et al.; Specific and Stable Intron–Factor Interactions Are Established Early during In Vitro Pre–mRNA Splicing. *Cell 43*, 131–142 (1985).

M. Kulka et al, PNAS, vol. 86 (Sep. 1989) pp. 6868–6872.

C. Stein et al, Science, vol. 261 (Aug. 20, 1993) pp. 1004–1012.

B. Tseng et al., Cancer Gene Therapy, vol. 1(1) (Mar. 1994) pp. 65–71.

E. Rapaport et al., PNAS, vol. 89 (Sep. 1992) pp. 8577–8580.

T. Gura, Science, vol. 270 (Oct. 27, 1995) pp. 575–577.

E. Uhlmann et al., Chem. Rev., vol. 90 (4) (Jun. 1990) pp. 543–584.

J. Milligan et al., J. Med. Chem, vol. 36 (14) (Jul. 9, 1993) pp. 1924–1937.

R. Kole et al. Adv. Drug Del. Rev. ('91) vol. 6: pp.271–286.

P. Furdan et al., Abstract, J. Cell. Bioch., Spd–13D (89) #K210.

F. Bennett et al., Mol. Pharm., vol. 41 (92) pp. 1023–1033.

*Primary Examiner*—Charles C. P. Rories
*Attorney, Agent, or Firm*—Bell, Seltzer, Park & Gibson

[57] ABSTRACT

A method of combatting aberrant splicing in a pre-mRNA molecule containing a mutation is disclosed. When present in the pre-mRNA, the mutation causes the pre-mRNA to splice incorrectly and produce an aberrant mRNA or mRNA fragment different from the mRNA ordinarily encoded by the pre-mRNA. The method comprises hybridizing an antisense oligonucleotide to the pre-mRNA molecule to create a duplex molecule under conditions which permit splicing. The antisense oligonucleotide is one which does not activate RNase H, and is selected to block a member of the aberrant set of splice elements created by the mutation so that the native intron is removed by splicing and the first mRNA molecule encoding a native protein is produced. Oligonucleotides useful for carrying out the method are also disclosed.

4 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:1:

GUCAGUGCCU AUCA                              14

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:2:

AUAGACUAAU AGGC                              14

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:3:

CAUUAUUGCC CUGAAAG                         17

( 2 ) INFORMATION FOR SEQ ID NO:4:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:4:

CCUCUUACCU CAGUUAC   17

( 2 ) INFORMATION FOR SEQ ID NO:5:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:5:

GCUAUUACCU UAACCCAG   18

( 2 ) INFORMATION FOR SEQ ID NO:6:

( i ) SEQUENCE CHARACTERISTICS:
 ( A ) LENGTH: 14 base pairs
 ( B ) TYPE: nucleic acid
 ( C ) STRANDEDNESS: single
 ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:6:

GCCUGACCAC CAAC   14

( 2 ) INFORMATION FOR SEQ ID NO:7:

( i ) SEQUENCE CHARACTERISTICS:
 ( A ) LENGTH: 14 base pairs
 ( B ) TYPE: nucleic acid
 ( C ) STRANDEDNESS: single
 ( D ) TOPOLOGY: linear ( i i ) MOLECULE TYPE: RNA (genomic)

( i v ) ANTI-SENSE: YES ( x i ) SEQUENCE DESCRIPTION: SEQ ID NO:7:

CCCAAAGACU AUCC   14

ANTISENSE OLIGONUCLEOTIDES WHICH COMBAT ABERRANT SPLICING AND METHODS OF USING THE SAME

This invention was made with government support under Grant No. GM32994 from the National Institutes of Health. The Government has certain rights to this invention.

CROSS-REFERENCE TO RELATED APPLICATIONS

This application is a divisional of pending prior file wrapper continuation application Ser. No. 08/379,079, filed Jan. 26, 1995, which is a continuation of abandoned parent case Ser. No. 08/062,471 filed May 11, 1993 the disclosure of which is incorporated by reference herein in its entirety.

FIELD OF THE INVENTION

The present invention relates to methods of combating aberrant splicing of pre-mRNA molecules and upregulating gene expression with antisense oligonucleotides, and antisense oligonucleotides useful for carrying out the same.

BACKGROUND OF THE INVENTION

The potential of oligonucleotides as modulators of gene expression is currently under intense investigation. Most of the efforts are focused on inhibiting the expression of targeted genes such as oncogenes or viral genes. The oligonucleotides are directed either against RNA (antisense oligonucleotides) (M. Ghosh and J. Cohen, *Prog. Nucleic Acid Res. Mol. Biol.* 42, 79 (1992); L. Neckers et al., *Crit. Rev. Oncog.* 3, 175 (1992)) or against DNA where they form triplex structures inhibiting transcription by RNA polymerase II (J. Hanvey et al., *Science* 258, 1481 (1992); W. McShan et al., *J. Biol. Chem.* 267, 5712 (1992); M. Grigoriev et al., *J. Biol. Chem.* 267, 3389 (1992); G. Duval-Valentin et al., *Proc. Natl. Acad. Sci. USA* 89, 504 (1992)). To achieve a desired effect the oligonucleotides must promote a decay of the preexisting, undesirable protein by effectively preventing its formation de novo. Such techniques are not useful where the object is to upregulate production of the native protein. Yet, in cases where the expression of a gene is downregulated because of mutations therein, a means for upregulating gene expression through antisense technology would be extremely useful.

SUMMARY OF THE INVENTION

The present invention provides means for using antisense oligonucleotides to upregulate expression of a DNA containing a mutation which would otherwise lead to downregulation of that gene by aberrant splicing of the pre-mRNA it encodes.

Accordingly, a first aspect of the present invention is a method of combatting aberrant splicing in a pre-mRNA molecule containing a mutation. When present in the pre-mRNA, the mutation causes the pre-mRNA to splice incorrectly and produce an aberrant mRNA or mRNA fragment different from the mRNA ordinarily resulting from the pre-mRNA. More particularly, the pre-mRNA molecule contains: (i) a first set of splice elements defining a native intron which is removed by splicing when the mutation is absent to produce a first mRNA molecule encoding a native protein, and (ii) a second set of splice elements induced by the mutation which define an aberrant intron different from the native intron, which aberrant intron is removed by splicing when the mutation is present to produce an aberrant second mRNA molecule different from the first mRNA molecule. The method comprises hybridizing an antisense oligonucleotide to the pre-mRNA molecule to create a duplex molecule under conditions which permit splicing. The antisense oligonucleotide is one which does not activate RNase H, and is selected to block a member of the aberrant second set of splice elements so that the native intron is removed by splicing and the first mRNA molecule encoding a native protein is produced.

A second aspect of the present invention is a method of upregulating expression of a native protein in a cell containing a DNA encoding the native protein. Which DNA further contains a mutation which causes downregulation of the native protein by aberrant splicing thereof. More particularly, the DNA encodes a pre-mRNA, the pre-mRNA having the characteristics set forth above. The method comprises administering to the cell an antisense oligonucleotide having the characteristics described above so that the native intron is removed by splicing and the native protein is produced by the cell.

A third aspect of the present invention is an antisense oligonucleotide useful for combatting aberrant splicing in a pre-mRNA molecule containing a mutation. The pre-mRNA molecule contains a first set and second set of splice elements having the characteristics set forth above. The antisense oligonucleotide comprises an oligonucleotide which (i) hybridizes to the pre-mRNA to form a duplex molecule; (ii) does not activate RNase H; and (iii) blocks a member of the aberrant second set of splice elements.

The foregoing and other objects and aspects of the present invention are discussed in detail in the drawings herein and the specification set forth below.

Figure 1:
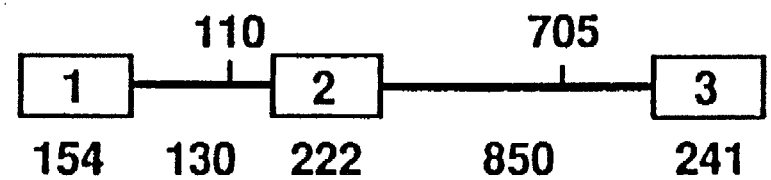
FIG. 1 shows the structure of pre-mRNAs. Boxes indicate exons; heavy lines, introns. Positions of the mutations (110 and 705) relative to nucleotide 1 of IVS 1 and IVS 2, respectively are shown above the HBΔ6 clone. Numbers below indicate the length, in nucleotides, of exons and introns. Antisense oligonucleotides are indicated by the numbered short bars below $\beta^{110}$ and $IVS2^{705}$ constructs, and splicing pathways by the dashed lines.
Figure 1:
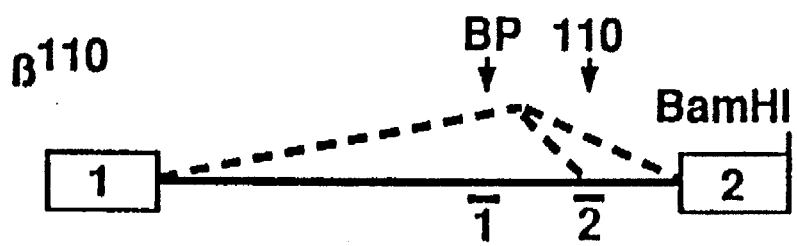
Figure 1:
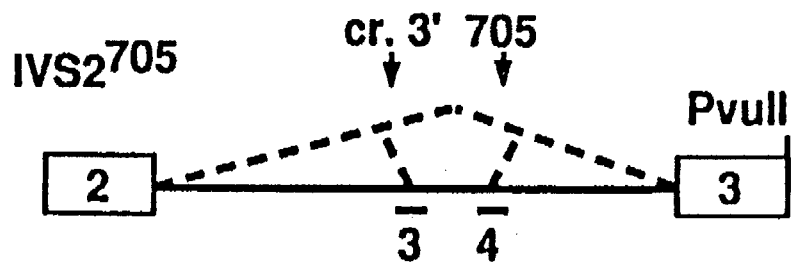

Lane 1 shows input RNA; lanes 2 and 3 show splicing of control transcripts (indicated at the top of the figure); lanes 4–8 and 9–13 show splicing of IVS2$^{705}$ pre-mRNA in the presence of oligonucleotide 3 and oligonucleotide 4, respectively. The amounts of the oligonucleotides in the reaction are indicated at the top. "?" on the left indicates apparent degradation product.

DETAILED DESCRIPTION OF THE INVENTION

Introns are portions of eukaryotic DNA which intervene between the coding portions, or "exons," of that DNA. Introns and exons are transcribed into RNA termed "primary transcript, precursor to mRNA" (or "pre-mRNA"). Introns must be removed from the pre-mRNA so that the native protein encoded by the exons can be produced (the term "native protein" as used herein refers to naturally occuring, wild type, or functional protein). The removal of introns from pre-mRNA and subsequent joining of the exons is carried out in the splicing process.

The splicing process is actually a series of reactions, mediated by splicing factors, which is carried out on RNA after transcription but before translation. Thus, a "pre-mRNA" is an RNA which contains both exons and intron(s), and an "mRNA" is an RNA in which the intron(s) have been removed and the exons joined together sequentially so that the protein may be translated therefrom by the ribosomes.

Introns are defined by a set of "splice elements" which are relatively short, conserved RNA segments which bind the various splicing factors which carry out the splicing reactions. Thus, each intron is defined by a 5' splice site, a 3' splice site, and a branch point situated therebetween. These splice elements are "blocked", as discussed herein, when an antisense oligonucleotide either fully or partially overlaps the element, or binds to the pre-mRNA at a position sufficiently close to the element to disrupt the binding and function of the splicing factors which would ordinarily mediate the particular splicing reaction which occurs at that element (e.g., binds to the pre-mRNA at a position within 3, 6, or 9 nucleotides of the element to be blocked).

The mutation in the native DNA and pre-mRNA may be either a substitution mutation or a deletion mutation which creates a new, aberrant, splice element. The aberrant splice element is thus one member of a set of aberrant splice elements which define an aberrant intron. The remaining members of the aberrant set of splice elements may also be members of the set of splice elements which define the native intron. For example, if the mutation creates a new, aberrant 3' splice site which is both upstream from (i.e., 5' to) the native 3' splice site and downstream from (i.e., 3' to) the native branch point, then the native 5' splice site and the native branch point may serve as members of both the native set of splice elements and the aberrant set of splice elements. In other situations, the mutation may cause native regions of the RNA which are normally dormant, or play no role as splicing elements, to become activated and serve as splicing elements. Such elements are referred to as "cryptic" elements. For example, if the mutation creates a new aberrant mutated 3' splice site which is situated between the native 3' splice site and the native branch point, it may activate a cryptic branch point between the aberrant mutated 3' splice site and the native branch point. In other situations, a mutation may create an additional, aberrant 5' splice site which is situated between the native branch point and the native 5' splice site and may further activate a cryptic 3' splice site and a cryptic branch point sequentially upstream from the aberrant mutated 5' splice site. In this situation, the native intron becomes divided into two aberrant introns, with a new exon situated therebetween. Further, in some situations where a native splice element (particularly a branch point) is also a member of the set of aberrant splice elements, it can be possible to block the native element and activate a cryptic element (i.e., a cryptic branch point) which will recruit the remaining members of the native set of splice elements to force correct splicing over incorrect splicing. Note further that, when a cryptic splice element is activated, it may be situated in either the intron or one of the adjacent exons. Thus, depending on the set of aberrant splice elements created by the particular mutation, the antisense oligonucleotide may be synthesized to block a variety of different splice elements to carry out the instant invention: it may block a mutated element, a cryptic element, or a native element; it may block a 5' splice site, a 3' splice site, or a branch point. In general, it will not block a splice element which also defines the native intron, of course taking into account the situation where blocking a native splice element activates a cryptic element which then serves as a surrogate member of the native set of splice elements and participates in correct splicing, as discussed above.

The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length.

Antisense oligonucleotides which do not activate RNase H can be made in accordance with known techniques. See, e.g., U.S. Pat. No. 5,149,797 to Pederson et al. (The disclosures of all patent references cited herein are to be incorporated herein by reference). Such antisense oligonucleotides, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense oligonucleotides which do not activate RNase H are available. For example, such antisense oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., C1–C4, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–1405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad. Sci. USA* 85, 5011–5015 (1988).

The methods, oligonucleotides and formulations of the present invention have a variety of uses. They are useful in any fermentation process where it is desired to have a means for downregulating expression of a gene to be expressed until a certain time, after which it is desired to upregulate gene expression (e.g., downregulate during the growth phase of the fermentation and upregulate during the production phase of the fermentation). For such use, the gene to be expressed may be any gene encoding a protein to be produced by fermentation so long as the gene contains a native intron. The gene may then be mutated by any suitable means, such as site-specific mutagenesis (see T. Kunkel, U.S. Pat. No. 4,873,192) to deliberately create an aberrant second set of splice elements which define an aberrant intron which substantially downregulates expression of the gene. The gene may then be inserted into a suitable expression vector and the expression vector inserted into a host cell (e.g., a eukaryotic cell such as a yeast, insect, or mammalian cell (e.g., human, rat)) by standard recombinant techniques. The host cell is then grown in culture by standard fermentative techniques. When it is desired to upregulate expression of the mutated gene, an antisense oligonucleotide, in a suitable formulation, which binds to a member of the aberrant second set of splice elements, is then added to the culture medium so that expression of the gene is upregulated.

The methods, oligonucleotides and formulations of the present invention are also useful as in vitro or in vivo tools to examine splicing in human or animal genes which are developmentally and/or tissue regulated. Such experiments may be carried out by the procedures described hereinbelow, or modification thereof which will be apparent to skilled persons.

The methods, oligonucleotides and formulations of the present invention are also useful as therapeutic agents in the treatment of disease involving aberrant splicing, such as β-thalassemia (wherein the oligonucleotide would bind to β-globin, particularly human, pre-mRNA), α-thalassemia (wherein the oligonucleotide would bind to α-globin pre-mRNA), Tay-Sachs syndrome (wherein the oligonucleotide would bind to β-hexoseaminidase α-subunit pre-mRNA), phenylketonuria (wherein the oligonucleotide would bind to phenylalanine hydroxylase pre-mRNA) and certain forms of cystic fibrosis (wherein the oligonucleotide would bind the cystic fibrosis gene pre-mRNA), in which mutations leading to aberrant splicing of pre-mRNA have been identified (See, e.g., S. Akli et al., *J. Biol. Chem.* 265, 7324 (1990); B. Dworniczak et al., *Genomics* 11, 242 (1991); L-C. Tsui, *Trends in Genet.* 8, 392 (1992)).

Examples of β-thalassemia which may be treated by the present invention include, but are not limited to, those of the $\beta^{110}$, $IVS1^5$, $IVS1^6$, $IVS2^{654}$, $IVS2^{705}$, and $IVS2^{745}$ mutant class (i.e., wherein the β-globin pre-mRNA carries the aforesaid mutations).

The term "antisense oligonucleotide" includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, $NH_4^+$, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polyga-lacturonic acid, and the like; and (d) salts formed from elemental anions such as chlorine, bromine, and iodine.

Formulations of the present invention comprise the antisense oligonucleotide in a physiologically or pharmaceutically acceptable carrier, such as an aqueous carrier. Thus, formulations for use in the present invention include, but are not limited to, those suitable for parenteral administration, including subcutaneous, intradermal, intramuscular, intravenous and intraarterial administration, as well as topical administration (i.e., administration of an aerosolized formulation of respirable particles to the lungs of a patient afflicted with cystic fibrosis). The formulations may conveniently be presented in unit dosage form and may be prepared by any of the methods well known in the art. The most suitable route of administration in any given case may depend upon the subject, the nature and severity of the condition being treated, and the particular active compound which is being used.

The present invention provides for the use of antisense oligonucleotides having the characteristics set forth above for the preparation of a medicament for upregulating gene expression in a patient afflicted with an aberrant splicing disorder, as discussed above. In the manufacture of a medicament according to the invention, the antisense oligonucleotide is typically admixed with, inter alia, an acceptable carrier. The carrier must, of course, be acceptable in the sense of being compatible with any other ingredients in the formulation and must not be deleterious to the patient. The carrier may be a solid or a liquid. One or more antisense oligonucleotides may be incorporated in the formulations of the invention, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation the antisense oligonucleotide may be contained within a lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[1-(2,3-dioleoyloxi) propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The dosage of the antisense oligonucleotide administered will depend upon the particular method being carried out, and when it is being administered to a subject, will depend on the disease, the condition of the subject, the particular formulation, the route of administration, etc. In general, intracellular concentrations of the oligonucleotide of from 0.05 to 50 μM, or more particularly 0.2 to 5 μM, are desired. For administration to a subject such as a human, a dosage of from about 0.01, 0.1, or 1 mg/Kg up to 50, 100, or 150 mg/Kg is employed.

The present invention is explained in greater detail in the following non-limiting examples. Nucleotide sequences are presented herein by single strand only, in the 5' to 3' direction, from left to right.

EXAMPLE 1

Structure and Construction of Pre-mRNAs

The construction and structure of various human β-globin pre-mRNA molecules is illustrated in FIG. 1. Boxes indicate exons; heavy lines, introns. Positions of the mutations (110 and 705) relative to nucleotide 1 of IVS 1 and IVS 2, respectively are shown above the HBΔ6 clone. Numbers below indicate the length, in nucleotides, of exons and introns. Antisense oligonucleotides (discussed in detail below) are indicated by the numbered short bars below $\beta^{110}$ and IVS2$^{705}$ constructs, and splicing pathways by the dashed lines. All pre-mRNAs were transcribed by SP6 RNA polymerase (M. Konarska et al., Cell 38, 731 (1984)) from appropriate fragments of human β-globin gene subcloned into the SP64 vector. HBΔ6 (A. Krainer et al., Cell 36, 993 (1984)) contains the whole human β-globin gene. The $^{110}$ construct contains exons 1 and 2 and was subcloned from the original thalassemic clone (R. Spritz et al., Proc. Natl. Acad. Sci. USA 78, 2455 (1981)). Before transcription, plasmids were linearized at the BamHI site. To construct the IVS2$^{705}$ plasmid, a fragment of HBΔ6 containing virtually the entire second exon, the entire second intron, and a major portion of the third exon was first subcloned in SP64 and subsequently subjected to site specific mutagenesis in accordance with known techniques (T. Kunkel et al., Methods Enzymol. 154, 367 (1987)) to introduce a T to G mutation at nucleotide 705 of the intron. Transcription was then carried out on a plasmid linearized at the PvuII site.

EXAMPLE 2

Synthesis of Antisense 2'O-methyl-Oligonucleotides

2'-O-methyl-Oligoribonucleotides for use in the examples described herein were synthesized in accordance with known techniques using reagents from Glen Research (Sterling, Va.) and purified in accordance with known techniques using the SUREPURE™ purification kit available from US Biochemicals.

2'-O-methyl-oligoribonucleotides produced were referred to as oligo 1 through oligo 5.

Oligo 1 (GUCAGUGCCUAUCA)(SEQ ID NO:1), complementary to nucleotides 82–95 of intron 1, is targeted against the normal branch point, and oligo 2 (AUAGACUAAUAGGC)(SEQ ID NO:2), complementary to nucleotides 103–116 of intron 1, against the aberrant 3' splice site created by $\beta^{110}$ mutation in intron 1 of the β-globin gene. Oligo 3 (CAUUAUUGCCCUGAAAG) (SEQ ID NO:3), complementary to nucleotides 573–589 of intron 2, is targeted against the cryptic 3' splice site at nucleotide 579 of the second intron and oligo 4 (CCUCUUACCUCAGUUAC) (SEQ ID NO:4), complementary to nucleotides 697–713, is targeted against the aberrant 5' splice site created by the mutation at nucleotide 705 in the second intron of IVS2$^{705}$ pre-mRNA. Oligo 5 (GCUAUUACCUUAACCCAG) (SEQ ID NO:5) is targeted against the aberrant 5' splice site created by the IVS2$^{654}$ mutation (nucleotides 643–660 of intron 2). Oligo 6 (GCCUGACCACCAAC) (SEQ ID NO:6) is targeted against the cryptic 5' splice site in exon 1of globin pre-mRNA (nucleotides −23 to −10 relative to nucleotide 1 of intron 1).

EXAMPLE 3

Reversal of Aberrant Splicing by an Antisense Oligonucleotide Targeted Against the Normal Branch Point of Human β-Globin Intron 1

In $\beta^{110}$- thalassemia, a form of the disease predominant in patients of Greek and Cypriot origin, an A to G mutation at nucleotide 110 of the first intron of human β-globin gene creates an additional, aberrant 3' splice site (R. Spritz et al., Proc. Natl. Acad. Sci. USA 78, 2455 (1981)). In spite of the presence of the normal 3' splice site, the aberrant site is preferentially used by the splicing machinery, resulting in an incorrectly spliced mRNA that contains 19 nucleotides of the intron sequence (FIG. 1). In cells transfected with $\beta^{110}$-globin allele (M. Busslinger et al., Cell 27, 289 (1981); Y. Fukumaki et al., Cell 28, 585 (1982)) or during splicing of its transcript in nuclear extracts (R. Reed and T. Maniatis, Cell 41, 95 (1985)) (see also FIG. 2, lane 2) correctly spliced mRNA constitutes only about 10% of the spliced product, consistent with the markedly reduced levels of normal hemoglobin observed in patients with this form of thalassemia. It was found that in $\beta^{110}$ pre-mRNA the aberrant 3' splice site recruits the normal branch point at nucleotide 93 of the intron, competing with the correct 3' splice site, and thereby prevents correct splicing (R. Reed and T. Maniatis, Cell 41, 95 (1985)). Significantly for this work, mutations inactivating the normal branch point activate a cryptic branch point at nucleotide 107 and result in splicing at the correct 3' splice site (Y. Zhuang and A. Weiner, Genes and Dev. 3, 1545 (1989)). Aberrant splicing cannot proceed due to the proximity of the cryptic branch point to the mutated 3' splice site at position 110.

To test whether antisense oligonucleotides targeted against the normal branch point sequence would force the splicing machinery to select the cryptic branch point and generate a correctly spliced mRNA, a 14 nucleotide long 2'-methyl-oligonucleotide (oligonucleotide 1, (SEQ ID NO:1)) was targeted against the branch point sequence in intron 1 of β-globin pre-mRNA. The 2'-O-methyl oligonucleotides were selected for this and subsequent experiments since they are resistant to nucleases and form stable hybrids with RNA that are not degraded by RNase H (H. Inoue et al., Nucleic Acids Res. 15, 6131 (1987); H. Inoue et al., FEBS Lett. 215, 327 (1987); B. Sproat et al., Nucleic Acids Res. 17, 3373 (1989)). Degradation by RNase H, seen for example when antisense oligodeoxynucleotides or their phosphorothioate derivatives are used, would destroy the substrate pre-mRNA and prevent any splicing.

Figure 2:
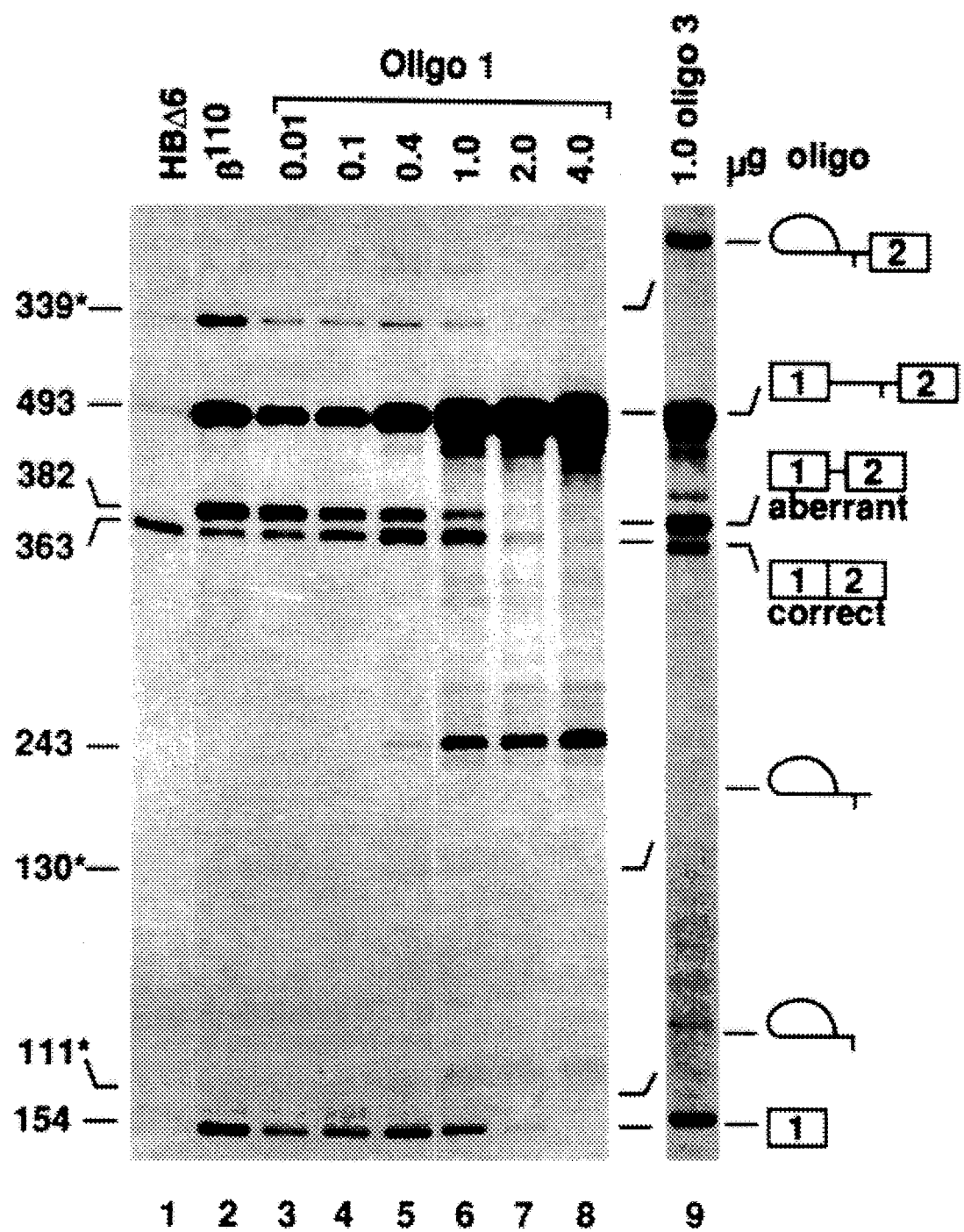
FIG. 2 shows the reversal of aberrant splicing by oligonucleotide 1 directed against the normal branch point in intron 1 of β-globin pre-mRNA. The structure of the products and intermediates is depicted on the right; their size in nucleotides is shown on the left. An asterisk denotes aberrant mobility of lariat-containing intermediates. The same designations are used in the subsequent figures. Lane 1 shows splicing of control HBΔ6 pre-mRNA; lane 2 shows splicing of $\beta^{110}$ pre-mRNA; lanes 3–8 show splicing of $\beta^{110}$ pre-mRNA in the presence of increasing amounts (indicated at the top of the figure) of oligonucleotide 1; lane 9 shows splicing of $\beta^{110}$ pre-mRNA in the presence of oligonucleotide 3, targeted to a sequence in intron 2 of β-globin pre-mRNA.

FIG. 2 shows the reversal of aberrant splicing by oligonucleotide 1 directed against the normal branch point in intron 1 of β-globin pre-mRNA. Splicing of p$^{32}$ labeled $\beta^{110}$ pre-mRNA (approximately 10$^5$ cpm per reaction, 25 fmoles) was carried out in vitro in HeLa cell nuclear extract for 2 hours, essentially as described (A. Krainer et al., Cell 36, 993 (1984); Z. Dominski and R. Kole, Mol. Cell. Biol. 12, 2108 (1992)) except that the volume of the reaction was doubled to 50 μl. Reaction products were analyzed on an 8% polyacrylamide sequencing gel and visualized by autoradiography. The structure of the products and intermediates is depicted on the right, their size in nucleotides is shown on the left. An asterisk denotes aberrant mobility of lariat-containing intermediates. Lane 1, splicing of control HBΔ6 pre-mRNA. Lane 2, splicing of $\beta^{110}$ pre-mRNA. Lanes 3–8, splicing of $\beta^{110}$ pre-mRNA in the presence of increasing amounts (indicated at the top of the figure) of oligonucleotide 1. Lane 9, splicing of $\beta^{110}$ pre-mRNA in the presence of oligonucleotide 3, targeted to a sequence in intron 2 of β-globin pre-mRNA.

Analysis of these data shows that in the control reaction without the oligonucleotide (FIG. 2, lane 2), the ratio of the incorrectly to correctly spliced products is approximately 9:1. Addition of oligonucleotide 1 at concentrations 0.01 to 1.0 μg per reaction (0.05–5 μM) causes dose dependent inhibition of aberrant splicing and induction of the correct splicing of the substrate (FIG. 2, lanes 3–6). At 1.0 μg of the oligonucleotide the ratio of spliced products is reversed to 1:5. The effect of the oligonucleotide is sequence specific since addition of 1 μg of an oligonucleotide targeted against the cryptic 3' splice site in the second intron of the β-globin gene (oligonucleotide 3, (SEQ ID NO:3); see also below) does not affect the original ratio of the spliced products (FIG. 2, lane 9). At 2.0 and 4.0 μg of oligonucleotide 1, splicing at both splice sites is inhibited and a 243-mer RNA fragment is generated (FIG. 2, lanes 7–8). This fragment accumulates only under splicing conditions, i.e. in the presence of ATP and other components of the splicing mixture, and most likely represents a product of cleavage at the site of the oligonucleotide's binding by an ATP dependent nuclease.

Figure 3:
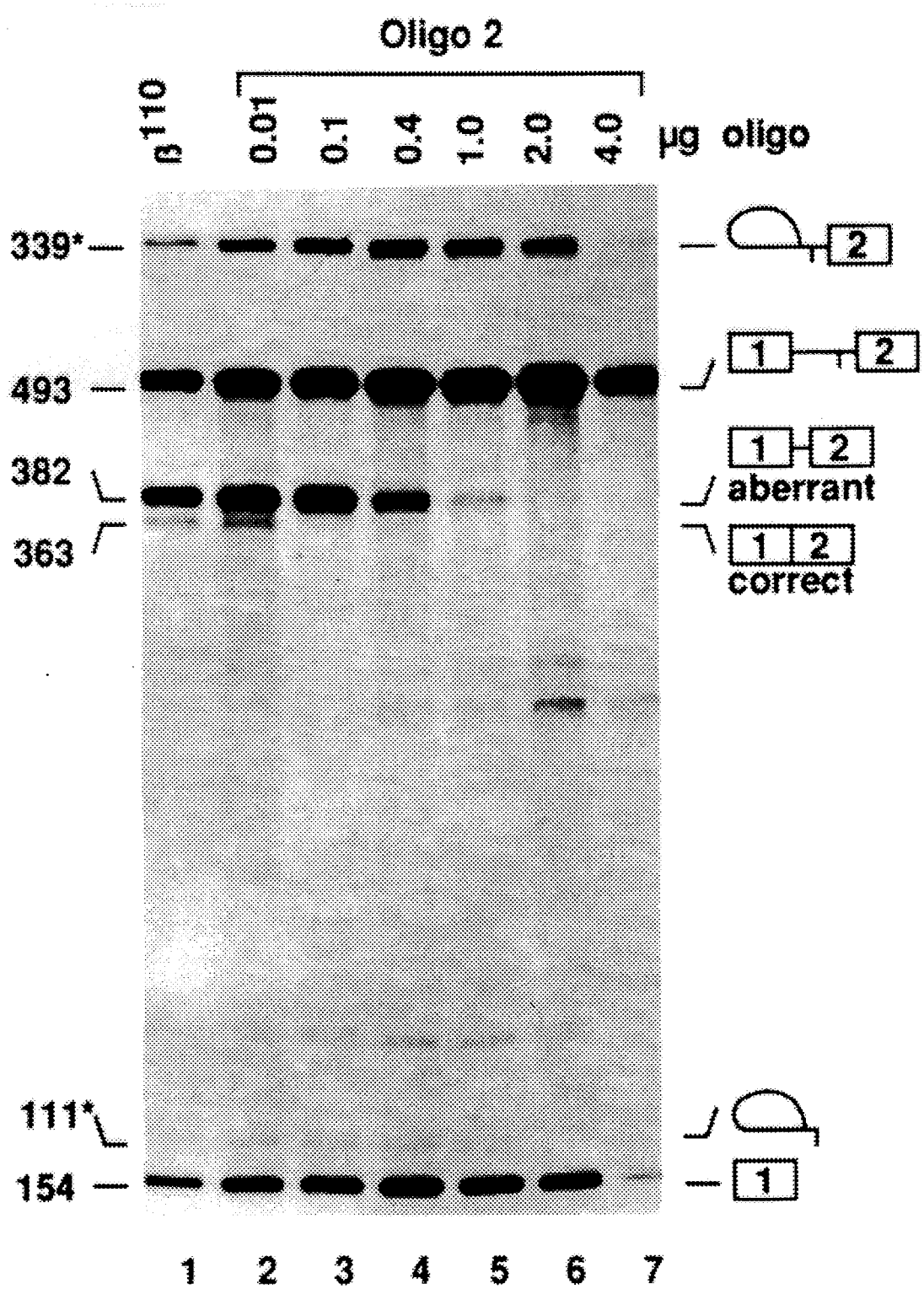
FIG. 3 shows the effects of oligonucleotide 2, directed against the aberrant 3' splice site in intron 1 of $\beta^{110}$ pre-mRNA. Lane 1 shows splicing of $\beta^{110}$ pre-mRNA; lanes 2–7 show splicing of $\beta^{110}$ pre-mRNA in the presence of increasing amounts (indicated at the top of the figure) of oligonucleotide 2.

The aberrant 3' splice site generated by the $\beta^{110}$ mutation also appears to be a target for reversal of aberrant splicing by an antisense oligonucleotide. Blocking of this sequence should be the simplest way of forcing the splicing machinery to use the original 3' splice site at the end of the intron. However, a 14-mer (oligo 2, (SEQ ID NO:2)) directed against the aberrant splice site was not effective; at increasing concentrations of the oligonucleotide accumulation of both spliced products was inhibited, the correct one being inhibited somewhat more efficiently (FIG. 3, lanes 2–5). Splicing was carried out under the same conditions as described in connection with FIG. 2. Interestingly, the first step of the splicing reaction, cleavage at the 5' splice site and formation of the lariat-exon intermediate, seems to be less affected by oligo 2 than the formation of the final spliced product. This is shown by the presence of these intermediates even when 1 or 2 μg of the oligonucleotide were added to the splicing reaction (FIG. 3, lanes 5–6). At 4 μg per reaction cleavage at the 5' splice site is inhibited (FIG. 3, lane 7).

The different effects of oligo 1 and oligo 2 reflect complex interactions among the oligonucleotides, the numerous splicing factors and sequence elements located in the stretch of 37 nucleotides between the normal branch point and the correct 3' splice site. Clearly, oligonucleotide 1, hybridized to the normal branch point at the 5' end of this region, prevents binding of the splicing factors to this sequence forcing them to select the cryptic branch point downstream. This leads to inhibition of aberrant splicing and induction of correct splicing of $\beta^{110}$ pre-mRNA. In contrast, hybridization of oligo 2 to its centrally located target sequence may hinder binding of a large number of splicing factors that assemble in this region and prevent any splicing. Note also that this oligonucleotide blocks a significant portion of the polypyrimidine tract that is essential for splicing to both the aberrant and the correct 3' splice sites. This is an alternative explanation why this oligonucleotide failed to restore the correct splicing pathway.

EXAMPLE 4

Reversal of Aberrant Splicing by Antisense Oligonucleotides Against the 5' and 3' Splice Sites of Human β-Globin Intron 2

Whether an aberrant 3' splice site can nevertheless be used as a target for reversal of incorrect splicing was further tested on pre-mRNA carrying a T to G mutation at position 705 of the second intron of human β-globin gene. This mutation (IVS2$^{705}$), found in Mediterranean thalassemia patients, creates an additional, aberrant 5' splice site 145 nucleotides upstream from the normal 3' splice site (C. Dobkin and A. Bank, *J. Biol. Chem.* 260, 16332 (1985)). During splicing, a cryptic 3' splice site is activated at position 579 of the intron resulting in the removal of nucleotides 1–578 and 706–850 as separate introns and incorporation of the remaining portion of the intron into the spliced product (FIG. 1). In this RNA the distances between each of the sequence elements involved in splicing exceed 100 nucleotides and no steric hindrance effects by the oligonucleotide should be expected.

Figure 4:
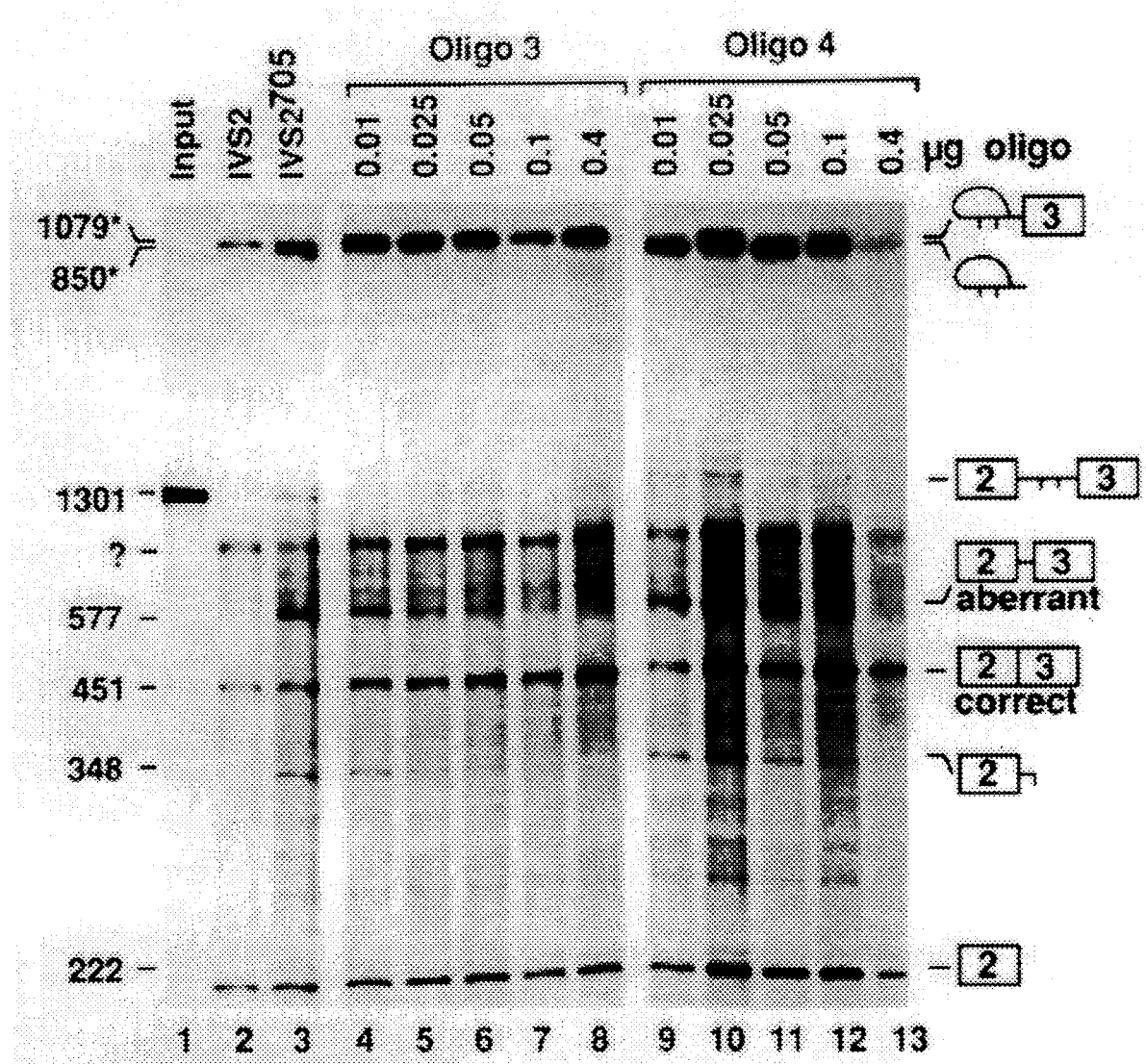
FIG. 4 shows the reversal of aberrant splicing of $IVS2^{705}$ pre-mRNA by oligonucleotide 3 directed against the cryptic 3' splice site and oligonucleotide 4 directed against the aberrant 5' splice site in intron 2 of the $IVS2^{705}$ pre-mRNA.

The reversal of aberrant splicing of IVS2$^{705}$ pre-mRNA by oligonucleotide 3 (SEQ ID NO:3) directed against the cryptic 3' splice site and oligonucleotide 4 (SEQ ID NO:4) directed against the aberrant 5' splice site in intron 2 of the IVS2$^{705}$ pre-mRNA is shown in FIG. 4. The conditions of the splicing reaction were the same as described in connection with FIG. 2 above, except that before use the RNA transcript was purified by electrophoresis on a 6% sequencing gel. Lane 1, input RNA. Lanes 2 and 3, splicing of control transcripts (indicated at the top of the figure). Lanes 4–8 and 9–13, splicing of IVS2$^{705}$ pre-mRNA in the presence of oligonucleotide 3 and oligonucleotide 4, respectively. The amounts of the oligonucleotides in the reaction are indicated at the top. "?" on the left indicates apparent degradation product.

The control transcript containing the second intron of normal β-globin pre-mRNA is spliced efficiently (FIG. 4, lane 2) generating the expected intermediates (the 5' exon and the large lariats) and the correctly spliced product, 451 nucleotides in length. Splicing of IVS2$^{705}$ pre-mRNA is also efficient and yields an additional spliced product 577 nucleotide long and an expected 348-mer intermediate, resulting from the aberrant splicing pathway caused by the mutation (FIG. 4, lane 3). The 1:2 ratio of correctly to incorrectly spliced RNAs is similar to that observed previously in vivo. Oligonucleotide 3 (FIG. 1) targeted at the activated cryptic 3' splice site at nucleotide 579 is very active, inducing dose dependent reversal of splicing to the correct splicing pathway (FIG. 4, lanes 4–8). At 0.1 and 0.4 μg of the oligonucleotide per reaction the reversal is virtually complete. Correct splicing is also obtained at similar concentrations of oligonucleotide 4 (FIG. 1) targeted against the aberrant 5' splice site created by the mutation at nucleotide 705 of the second intron (FIG. 4, lanes 9–13). At 1 and 2 μg per reaction, either oligonucleotide had no additional effects; at 4 μg per reaction (20 μM) all splicing is inhibited (not shown). Additional bands, including a strong band marked by "?" in a figure are most likely due to nuclease degradation of the long (1301 nucleotides) pre-mRNA.

These results show that the cryptic 3' splice site as well as the mutated 5' splice site provide suitable targets for specific reversal of aberrant splicing. Similar effects of oligonucleotides 3 and 4 suggest that there are no major differences in their accessibilities to the target splice sites. Both oligonucleotides are approximately 10 times more effective than oligonucleotide 1 used in the experiments shown in FIG. 2. This higher efficiency may be due to several factors. Oligonucleotides 3 and 4 are three nucleotides longer than oligonucleotide 1 and may form more stable hybrids with RNA. They block aberrant splice sites, allowing the splicing machinery to use the correct splice sites and, presumably, the correct branch point. In contrast, in $\beta^{110}$ pre-mRNA oligonucleotide 1 forces the splicing machinery to use a suboptimal cryptic branch point sequence, which may result in relatively inefficient generation of correctly spliced mRNA. In experiments shown in FIG. 4 the long input pre-mRNA is barely detectable after 2 hours of the reaction, suggesting its instability. Thus, although the molar concentrations of the oligonucleotides were essentially the same as in previous experiments they may have been in greater excess over the substrate pre-mRNA.

In the experiments presented above the oligonucleotides were added simultaneously with the other components of the splicing reaction. Prehybridization of the oligonucleotides with the pre-mRNA did not increase their efficiency and oligonucleotides added 15 minutes after the start of the reaction, i.e. after splicing complexes had a chance to form (B. Ruskin and M. Green, *Cell* 43, 131 (1985)), were almost as effective (data not shown). These results indicate that oligonucleotides containing the 2'-O-methyl modification are able to compete effectively for their target sequences with the splicing factors. The high activity of these compounds is most likely due to their strong hybridization to RNA.

EXAMPLE 5

Reversal of Aberrant Splicing With an Antisense Oligonucleotide Which Blocks the Cryptic 3' Splice Site the IVS1-5 and IVS1-6

This experiment is carried out essentially as described above, except that the thalassemic mutations are the IVS1-5 and IVS1-6 mutations, in which the authentic 5' splice site of IVS1 is mutated. Aberrant splicing resulting in thalassemia is apparently due to the fact that mutations IVS1-5 and IVS1-6 weaken the 5' splice site and allow the cryptic splice site located 16 nucleotides upstream to successfully compete for the splicing factors. In this experiment we test whether an oligonucleotide antisense to the cryptic splice site may revert aberrant splicing back to the mutated 5' splice site and restore correct splicing in spite of the mutations, since splice sites similar to the mutated ones appear functional in other pre-mRNAs. The oligonucleotide employed is oligo 6 (SEQ ID NO:6), a 2-O-methyl-ribooligonucleotide produced as described in Example 2 above.

EXAMPLE 6

Reversal of Aberrant Splicing With an Antisense Oligonucleotide Which Blocks the Aberrant 5' Splice Site of the IVS2$^{654}$ Mutation These experiments are carried out essentially as described above, except that the human β-globin pre-mRNA containing the IVS2$^{654}$ mutation is employed, and oligo 5 (SEQ ID NO:5) is employed.

The IVS2$^{654}$ mutation, frequently identified in thalassemic individuals of Chinese origin, affects splicing by creating an additional 5' splice site at nucleotide 653 and activating the common cryptic 3' splice site at nucleotide 579 of intron 2. The efficiency of aberrant splicing of IVS2$^{654}$ pre-mRNA is higher than that for IVS2$^{705}$ pre-mRNA and only small amounts of correctly spliced product, relative to the aberrant one, are detectable during splicing in vitro. In spite of the high efficiency of aberrant splicing, oligo 3, targeted against the cryptic 3' splice site, as well as oligo 5, targeted against the aberrant 5' splice site, restored correct splicing efficiently at concentrations similar to those described above. At 2 μM concentration of either oligonucleotide the correctly spliced product accumulates and the aberrant product is virtually undetectable (data not shown).

EXAMPLE 7

Reversal of Aberrant Splicing by Antisense Oligonucleotide Which Blocks the Human β-Globin Intron 1 Branch Point This experiment is carried out essentially as described above to restore correct splicing in β-110 mutant pre-mRNA, except the oligonucleotide binds to a sequence located just upstream from the native branch point sequence of intron 1 of β-globin gene (nucleotides 75–88). The sequence of the oligonucleotide is: CCCAAAGACUAUCC (SEQ ID NO:7). Correct splicing is restored.

EXAMPLE 8

Construction of Cell Lines Expressing Thalassemic Human β-Globin pre-mRNA

A series of stable cell lines are constructed by transfecting HeLa cells and CHO cells with thalassemic globin genes cloned under the cytomegalovirus (CMV) immediate early promoter. The genes include IVS1-110, IVS2-654 and IVS1-5 mutation.

Stable cell lines are obtained in accordance with standard techniques. See, e.g., Current Protocols in Molecular Biology (P. Ausubel. et al. eds. 1987). Briefly, cells are cotransfected with plasmids carrying thalassemic globin genes under the CMV promoter and plasmids carrying the neomycin resistance gene as a selectable marker (pSV2neo). Transfection is either by electroporation, (Z. Dominski and R. Kole, *Mol. Cel. Biol.* 11: 6075–6083 (1991); Z. Dominski and R. Kole, *Mol. Cell. Biol.* 12: 2108–2114 (1992)), or by the calcium phosphate method. Cells are plated and after 24–48 hours challenged with selective medium containing G418. Surviving colonies are expanded and assayed for expression of thalassemic globin mRNA as follows.

Total RNA is isolated from approximately $10^5$ cells using a commercial Tri-Reagent (Molecular Research Center, Cincinnati, Ohio) following manufacturer's protocol. This method allows for easy processing of a large number of small samples and gives high yields of good quality RNA. The splicing patterns are analyzed by RT-PCR using rTth polymerase and following the manufacturers protocol (Perkin Elmer). No more than 1–5% of isolated RNA is required for detection of spliced RNA in transiently transfected cells, thus the method is sufficiently sensitive for easy detection in stable cell lines. The reverse transcriptase step is carried out with a 3' primer that hybridizes to the aberrant sequences in thalassemic mRNA and spans the splice junction. This assures that the contaminating DNA and normal globin RNA are not detected and do not interfere with the assay. The cloned cell lines that express thalassemic pre-mRNA are used for treatment with antisense 2'-O-methyl-oligonucleotides as described below.

EXAMPLE 9

Administration of Antisense Oligonucleotides In Cell Culture

Cells produced in Example 8 above are grown in 24 well culture dishes containing 200 μl of media per well. $2\times10^4$ cells are seeded per well and when attached they are treated with 200 μl of media containing up to 50 μM concentration of antisense oligonucleotides. Cells are cultured up to 4 days in the presence of the oligonucleotide before reaching confluence ($2-3\times10^5$ cells). Since 2'-O-methyl oligonucleotides are very stable in serum containing media, medium is changed no more than every two days. The 50 μM (40 μg per well) concentration of the oligonucleotide represents 100 fold excess over that required to elicit efficient restoration of splicing in vitro. Even at this concentration a single oligonucleotide synthesis at 1 μmole scale, yielding 1–1.6 mg of the oligonucleotide, provides sufficient material for 25 to 40 samples.

In an alternative approach cells are pretreated with Lipofectin™ reagent (DOTMA, from BRL) at a concentration of 10 μg/ml before addition of oligonucleotides, in accordance with known techniques. (C. Bennett et al., *Mol. Pharm.* 41: 1023–1033 (1992)).

After treatment total RNA is isolated as above and assayed for the presence of correctly spliced mRNA by RT-PCR. Amplification of primers is carried out in the presence of alpha-P32 labeled ATP to increase sensitivity of detection and reduce the number of cycles to 15.

The foregoing examples are illustrative of the present invention, and are not to be construed as limiting thereof. The invention is defined by the following claims, with equivalents of the claims to be included therein.

That which is claimed is:

1. An oligonucleotide consisting of the nucleotide sequence shown as SEQ ID NO: 1, 3, 4, 5, or 7, which oligonucleotide does not activate RNase H.

2. An antisense oligonucleotide according to claim 1, wherein said oligonucleotide contains a modified internucleotide bridging phosphate residue selected from the group consisting of methyl phosphonates, methyl phosphonothioates, phosphoromorpholidates, phosphoropiperazidates, and phosphoramidates.

3. An antisense oligonucleotide according to claim 1, wherein said antisense oligonucleotide contains a nucleotide having a lower alkyl substituent at the 2' position thereof.

4. An antisense oligonucleotide according to claim 1 in a lipid vesicle.

* * * * *